United States Patent [19]
Stark et al.

[11] Patent Number: 5,651,941
[45] Date of Patent: Jul. 29, 1997

[54] SAMPLE TUBE CARRIER

[75] Inventors: William A. Stark, Costa Mesa; Kempton H. Hardiman, Mission Viejo; Richard A. Scribner, Fullerton; John Mazza, El Toro, all of Calif.

[73] Assignee: Dade International Inc., Deerfield, Ill.

[21] Appl. No.: 488,894

[22] Filed: May 17, 1995

Related U.S. Application Data

[63] Continuation of Ser. No. 906,257, Jun. 29, 1992, abandoned.

[51] Int. Cl.⁶ .................................................. B01L 9/00
[52] U.S. Cl. ................ 422/104; 422/102; 422/99; 220/676; 220/682
[58] Field of Search ....................... 422/102, 104, 422/99, 103; 220/670–671, 676, 680–682

[56] References Cited

U.S. PATENT DOCUMENTS

| | | | |
|---|---|---|---|
| 1,147,856 | 7/1915 | Gilchrist | 248/145.6 |
| 2,215,411 | 8/1940 | Sebring | 248/311.2 |
| 2,963,167 | 12/1960 | Norman | 211/74 |
| 3,194,426 | 7/1965 | Brown, Jr. | 220/23.4 |
| 3,263,078 | 7/1966 | Thackara et al. | 378/79 |
| 3,286,583 | 11/1966 | Ferrari | 422/104 |
| 3,317,081 | 5/1967 | Cornelius | 206/144 |
| 3,350,946 | 11/1967 | Isreeli | 73/864.91 |
| 3,521,785 | 7/1970 | Bergmann et al. | 220/23.4 |
| 3,526,480 | 9/1970 | Findl et al. | 422/66 |
| 3,533,744 | 10/1970 | Unger | 436/63 |
| 3,538,962 | 11/1970 | Gilson | 141/131 |
| 3,545,932 | 12/1970 | Gilford | 422/73 |
| 3,574,064 | 4/1971 | Binnings et al. | 435/293 |
| 3,617,222 | 11/1971 | Matte | 436/48 |
| 3,713,771 | 1/1973 | Taylor et al. | 422/104 |
| 3,728,227 | 4/1973 | Elson et al. | 435/291 |
| 3,825,410 | 7/1974 | Ragshawe | 436/57 |
| 3,882,619 | 5/1975 | Durand et al. | 422/104 |
| 3,883,308 | 5/1975 | Matte | 422/64 |
| 3,897,216 | 7/1975 | Jones | 422/104 |
| 3,900,289 | 8/1975 | Liston | 436/54 |
| 3,916,157 | 10/1975 | Roulette et al. | 422/104 |
| 3,926,514 | 12/1975 | Costanza et al. | 353/113 |
| 3,977,794 | 8/1976 | Liedholz | 356/244 |
| 3,993,452 | 11/1976 | Moulding | 422/104 |
| 4,019,638 | 4/1977 | Miller | 211/74 |
| 4,039,288 | 8/1977 | Moran | 422/65 |
| 4,047,820 | 9/1977 | Soodak et al. | 356/244 |
| 4,066,412 | 1/1978 | Johnson et al. | 422/65 |
| 4,142,863 | 3/1979 | Covington et al. | 422/63 |
| 4,160,803 | 7/1979 | Potts | 422/104 |
| 4,207,289 | 6/1980 | Weiss | 422/104 |

(List continued on next page.)

FOREIGN PATENT DOCUMENTS

| | | |
|---|---|---|
| 0 125 996 | 11/1984 | European Pat. Off. . |
| 3809867 | 10/1988 | European Pat. Off. . |
| 0 295 047 | 12/1988 | European Pat. Off. . |
| 313977 | 5/1989 | European Pat. Off. . |
| 0 414 644 | 2/1991 | European Pat. Off. . |
| 1133819 | 11/1968 | United Kingdom . |

*Primary Examiner*—Timothy McMahon
*Assistant Examiner*—Hien Tran
*Attorney, Agent, or Firm*—Terry L. Miller; Kurt A. MacLean

[57] ABSTRACT

A self-adjusting linkable carrier for sample tubes, cuvettes, cells and the like comprising a longitudinally symmetrical vertically oriented polygonal body having two pairs of orthogonally disposed opposed vertical faces and a horizontal bottom sliding surface is disclosed. The top surface of the body is provided with a central bore opening into a vertical cavity adapted to releasably receive and retain a wide variety of sample tube configurations in a stable vertical orientation. Machine readable indicia may be provided on the external surface and vertical slots are provided in each external face to provide access to the central vertical cavity. A releasably locking horizontally aligned dovetail feature is provided to link adjacent carriers into conveniently handled racks or magazines which may be assembled and disassembled by machine. Additional horizontally sliding indexing elements are provided to facilitate the stable storage and transport of the carrier.

28 Claims, 3 Drawing Sheets

U.S. PATENT DOCUMENTS

| | | | |
|---|---|---|---|
| 4,224,032 | 9/1980 | Glover et al. | 422/65 |
| 4,224,033 | 9/1980 | Hansen et al. | 422/81 |
| 4,269,803 | 5/1981 | Jessop | 422/63 |
| 4,296,069 | 10/1981 | Smith et al. | 422/64 |
| 4,296,070 | 10/1981 | Montalto et al. | 422/65 |
| 4,323,536 | 4/1982 | Columbus | 422/56 |
| 4,339,221 | 7/1982 | Mitzel et al. | 414/114 |
| 4,357,301 | 11/1982 | Cassaday et al. | 422/64 |
| 4,396,286 | 8/1983 | Shofner et al. | 356/243 |
| 4,456,690 | 6/1984 | Cais et al. | 436/500 |
| 4,512,952 | 4/1985 | Blanding et al. | 422/63 |
| 4,517,851 | 5/1985 | Tice | 422/102 |
| 4,518,076 | 5/1985 | Feisel et al. | 198/648 |
| 4,534,465 | 8/1985 | Rothermel et al. | 422/104 |
| 4,587,221 | 5/1986 | Cais et al. | 33/53 |
| 4,661,711 | 4/1987 | Harjunmaa | 250/458.1 |
| 4,672,038 | 6/1987 | Jaekel et al. | 435/291 |
| 4,750,837 | 6/1988 | Gifford et al. | 356/417 |
| 4,801,428 | 1/1989 | Homolko et al. | 422/102 |
| 4,807,421 | 2/1989 | Araki et al. | 53/167 |
| 4,815,978 | 3/1989 | Mazza et al. | 435/4 |
| 4,843,021 | 6/1989 | Noguchi et al. | 436/533 |
| 4,849,176 | 7/1989 | Sakagami | 422/64 |
| 4,849,177 | 7/1989 | Jordan | 422/64 |
| 4,857,471 | 8/1989 | Salzman et al. | 436/43 |
| 4,861,163 | 8/1989 | Bach | 356/417 |
| 4,889,612 | 12/1989 | Geist et al. | 204/416 |
| 4,929,426 | 5/1990 | Bodai et al. | 422/63 |
| 4,937,049 | 6/1990 | Burrett et al. | 422/63 |
| 4,944,924 | 7/1990 | Mawhirt et al. | 422/104 |
| 5,002,199 | 3/1991 | Frahm | 220/670 |
| 5,112,574 | 5/1992 | Horton | 422/102 |
| 5,127,541 | 7/1992 | Wakatake | 220/737 |
| 5,128,105 | 7/1992 | Berthold et al. | 422/104 |
| 5,137,693 | 8/1992 | Mawhirt | 422/104 |
| 5,139,746 | 8/1992 | Rabenecker | 422/104 |

SAMPLE TUBE CARRIER

This application is a continuation of application Ser. No. 07/906,257, filed Jun. 29, 1992, now abandoned.

FIELD OF THE INVENTION

The present invention relates generally to devices for manipulating individual specimens to be processed by automated apparatus. More particularly, the present invention relates to linkable sample carriers for storing and transporting specimen sample tubes, cells, cuvettes and the like for use in conjunction with automated analysis apparatus. The present invention is particularly useful in automated chemical analyzers and related equipment for use in examining and analyzing blood, physiological fluids, and other biological samples.

BACKGROUND OF THE INVENTION

A wide variety of automated clinical analyzers are known in the art and widely used in hospitals, clinics, and research laboratories. A particularly popular example of such a device is the multi-channel type analyzer in which a series of different tests are performed simultaneously and in parallel with one another. The typical multi-channel analyzer generally utilizes liquid or solid reagents to react with a particular constituent present in a sample in conjunction with a photo-optical system to determine the rate of reaction, constituent concentration in the sample, and the like.

The usual method employed for performing these photometric procedures is to place the sample solution in a small cell, tube, or cuvette provided with transparent walls and interposing the sample solution between a light source and a photosensitive detecting element. In order to perform multiple tests simultaneously on each sample most contemporary multi-channel analyzers utilize a number of small sample aliquots taken from a larger sample volume originally supplied to the machine. These larger sample specimens are stored and manipulated in cells or tubes of varying size and configuration, the most common being round, oblong sample or test tubes while others include rectangular or square cells and alternative configurations. This form of individualized sample processing avoids the problem of cross-contamination previously associated with earlier flow-through type devices.

Although multi-channel automated analyzers have received wide acceptance, there are certain drawbacks associated with their use. For example, to provide precise and accurate handling of the sample tubes it is necessary to position and align the tubes within the apparatus accurately so that the various sample aliquots may be automatically and consistently removed as needed. Additionally, in order to correlate the multiple test results properly with the appropriate samples an accurate identification and tracking systems must be utilized. As a result, a variety of specialized sample cells and identification means have been developed in the art. Unfortunately, the majority are machine specific which limits the applicability of the particular analyzer to only those samples which are properly packaged in the appropriate sample tubes or modified with potentially clumsy adapters. Additionally, relatively highly trained personnel are required to operate these machines effectively, as simple mistakes can render entire sample runs useless.

In order to handle the transportation, alignment, and tracking needs of large sample batches effectively, most prior art multi-channel analyzers utilize sample tube racks or carrousels which are organized and loaded with sample tubes prior to positioning within the analyzer input areas. Though these racks provide a degree of convenience in connection with sample tube handling and bulk storage and identification, they make it virtually impossible to interrupt the analyzer apparatus once a sequence has been started and also impose a degree of restriction with respect to the handling of individual sample tubes.

Another significant disadvantage associated with these types of automated analyzing equipment is their inability to perform emergency "stat" tests due to their relatively long and complex setup times and the resultant inability to interrupt the order and flow of the organized samples. Similarly, though a relatively rare occurrence, if a sample tube should fracture or leak the entire sample run may be jeopardized if the machine cannot be interrupted without losing track of the samples.

An alternative approach to sample tube handling has been the development of individual sample tube carriers which may be stored in racks and loaded into conveyor lines. For example, U.S. Pat. No. 3,916,157, issued Oct. 28, 1975, illustrates a specimen carrier for test tubes that is provided with a slotted base that will engage with a geared conveyor track for transporting the carrier through an automated analyzer. Additionally, each carrier is provided with its own identification tag so that the sample carrier can be identified. An alternative sample container is disclosed in U.S. Pat. No. 3,350,946, issued Nov. 7, 1967. This system utilizes a vial with a vertical T-shaped flange that enables it to be inserted into a carousel. A machine readable tag is attached to the vial for tracking purposes. Similarly, U.S. Pat. No. 4,944,924, issued Jul. 31, 1990, also discloses a test tube holder that pivots along a belt-like conveyor.

Though effective at overcoming some of the earlier drawbacks associated with bulky carrousels and similar sample tube handling apparatus, these devices fail to address the need for an adaptable sample tube carrier that will readily self-adjust to handle a wide variety of sample tube sizes and configurations without jeopardizing machine performance. Moreover, there remains a need to provide a sample carrier system that will allow an operator to conveniently manipulate or store individual samples as well as bulk quantities of individual samples.

An additional need exists for a sample tube carrier that will readily interface with an automated analyzer system yet allow for sample input interruption and "stat" tests. A need also exists for a sample tube carrier that will protect a sample tube from damage yet allow a defective or broken tube to be removed without interrupting the process of an analyzer apparatus. Moreover, it would be of significant benefit to the medical field and related professions to provide a sample carrier which simplified the level of skill necessary to effectively operate an automated processing apparatus.

Accordingly, it is an object of the present invention to provide a sample tube carrier that can be releasably linked with identical carriers into stable rows and racks for initial sample handling and transport yet which will readily interface with automated conveyor loading systems in both individual and bulk formats for automatic processing.

It is an additional object of the present invention to provide a sample tube carrier that will self-adjust to releasably receive and retain sample tubes or cells of varying sizes and configurations.

It is yet an additional object of the present invention to provide a sample tube carrier that will automatically align the vertical centerline of a sample tube with that of the sample tube carrier so that sample aliquots can be drawn accurately and repeatably from the center of the sample tube.

It is a further object of the present invention to provide a sample tube carrier that will readily interface with modern automated analysis equipment yet will relieve the human operator from complex handling and record keeping functions.

It is an additional object of the present invention to provide a sample carrier that is robust, simple and inexpensive to manufacture and operate, and which provides enhanced operator safety.

SUMMARY OF THE INVENTION

These and other objects are achieved by the sample tube carrier of the present invention which, in accordance with broad structural aspects thereof, provides a linkable carrier that will securely retain, center, and transport a wide variety of sample tube shapes and sizes without adapters or complex adjustable features. Moreover, the sample tube carrier of the present invention is uncomplicated, robust, lightweight, safe in operation, and easy to operate making it simple and convenient to use with even relatively unskilled operators. Further, the sample tube carrier of the present invention can be linked to form individual rows or rack groupings for bulk sample manipulation and storage yet provides for a simple, flexible format automated interface with processing apparatus conveyors and transport means.

More specifically, in accordance with broad structural aspects of the invention, a linkable sample tube carrier is formed of a lightweight, preferably plastic carrier body shaped as a longitudinally symmetrical vertically oriented oblong polygon. The polygon may be formed from a unitary or multi-piece body of strong lightweight material such as plastic or metal and is shaped to have at least four generally planar external side surfaces forming at least two orthogonally or perpendicularly disposed pairs of generally rectangular, mutually opposed vertical faces. The base of the body is a sliding surface, preferably planar, while the top surface is provided with a central bore extending into a vertical cavity formed along at least a portion of the longitudinal (vertical) axis of the body member. This vertical cavity or bore is adapted to releasably receive and retain a variety of sample tubes in proper orientation for handling and processing through the utilization of self-adjusting tube positioning means and self-centering tube aligning means.

In the preferred embodiment of the present invention the self-adjusting positioning means for releasably receiving and retaining the sample tube within the vertical cavity is formed of a plurality of opposed biasing springs which are positioned about the central bore in the top surface of the polygonal body and extend into the vertical cavity at an angle to a position within the cavity and spaced away from its sides. The self-centering means may be formed of a generally funnel shaped conical or parabolic depression provided in the base of the vertical cavity or by inclined planes arranged at the cavity base for engaging the bottom of the sample tube inserted into the cavity.

Thus, in operation a sample tube is simply inserted along the vertical axis of the polygonal body from the top opening or bore into the vertical cavity where the opposed biasing springs will self-adjust to the dimensions of the tube and, in conjunction with the funnel shaped base of the bore engaging the bottom of the tube, will center the tube in a secure, vertically oriented alignment within the polygonal body. Removal of the sample tube is similarly a simple matter of pulling the tube out of the vertical bore as there are no clips, clamps or adapters to interfere with or complicate this function. In this manner, the sample tube carrier of the present invention is able to securely receive and retain a wide variety of sample tubes having cross-sectional diameters or faces ranging from approximately 7 millimeters to 17 millimeters. Additionally, tube length can vary from, for example, 50 millimeters to 110 millimeters as the polygonal body is open ended.

Preferably, each of the generally rectangular opposed faces forming the external side surfaces of the polygon is provided with a vertical slot which, intersects the vertical cavity. This slot enables an automated photometric analyzing apparatus to view the sample tube disposed within the vertical bore of the sample carrier without interference. Preferably, each slot will extend from the top surface of the polygonal body to the base of the vertical bore. However, shorter slot lengths may be utilized as desired to avoid interference with the self-adjusting positioning springs and self-centering base of the bore. Because of the positioning of the vertical slots the opposed biasing spring members are preferably located at each intersection of adjacent polygonal faces as this provides sufficient body material to securely mount each biasing spring. This biasing spring location and orientation also functions to eliminate any projecting springs or surfaces which may snag operator clothing or possibly erroneously engage projecting surfaces as the sample carrier is transported or manipulated. As a result, this construction facilitates the safe and simple operation of the present invention.

In order to provide the sample tube carrier with the ability to interface with processing apparatus conveyors, tracks, and the like as well as to link with adjacent carriers to form conveniently manipulated carrier racks or chains, each sample carrier is provided with means for releasably linking two adjacent carriers as well as means for slidingly engaging adjacent carriers or processing apparatus.

For example, one pair of opposing vertical faces can be provided with an enlarged head projecting member or members such as a dovetail on one face and a correspondingly aligned and configured mating groove in the other opposing face. The groove and enlarged head or dovetail are horizontally aligned to allow adjacent carriers to be conveniently linked through a simple horizontal sliding motion where the projecting member is engaged into the corresponding mating groove of the adjacent carrier. Once in position a biasing spring located in the groove will releasably lock the enlarged head member of the adjacent carrier in position. In this manner, an endless chain of linked sample carriers can be created from any number of carriers. However, for convenient manipulation of sample tube groupings it is suggested that from five to ten carriers be linked into a row which will remain together without external support. Additionally, because of the relatively flat bottom sliding surfaces each row can be readily maneuvered on a flat table, trough, or conveyor chute.

Further, it is preferred that the second pair of opposing vertical faces be provided with horizontally engaging sliding means for indexing adjacent carriers, carrier rows, or with processing apparatus. For example, an exemplary horizontally engaging sliding means for indexing may be formed from a horizontally aligned member projecting from one of the second pair of opposed rectangular faces while a correspondingly aligned horizontal groove is provided in the second generally rectangular face of this second pair of opposed faces.

This tongue and groove arrangement does not require an enlarged head like the previously discussed releasable linking means. Rather, the horizontal tongue and groove of the sliding means for indexing enables individual sample carriers or linked carrier rows to slide relative to one another while maintaining horizontal positioning. Additionally, this feature of the present invention enables linked rows to be indexed into stable bulk racks of multiple sample tubes for convenient storage or bulk handling.

To facilitate the automated manipulation, identification and record keeping of the sample tube carriers, at least one of the external faces may be provided with machine readable indicia such as a bar code. Preferably, it is contemplated that the sample tubes (which do not form a part of the present invention but are used in conjunction with it) will include their own machine readable indicia or bar codes as this will enable the individual sample tubes and carriers to be identified, tracked and correlated during processing or storage. This also eliminates the need for manual tracking of each carrier and sample tube individually.

If desired, at least one of the second pair of opposing faces provided with the horizontally engaging sliding members may also be provided with an indexing notch such as a conical hole. This will enable an automated processing apparatus to positively slide and decouple the horizontal engaging means so that individual sample carriers can be linked and unlinked from a rack, row or chain of carriers using a simple plunger or slide apparatus to slide the carrier horizontally along its bottom sliding surface relative to a stationary adjacent carrier.

Other features and advantages of the present invention will become apparent from the following detailed description thereof, taken in conjunction with the accompanying drawings which illustrate, by way of example, the principles of the present invention.

DETAILED DESCRIPTION

The sample tube carrier of the present invention is applicable to a wide variety of automated specimen manipulation or processing apparatus and provides for the safe, simple, convenient and adaptable storage and manipulation of sample specimens to a degree previously unobtainable by the prior art. As such, the linkable sample tube carriers of the present invention are particularly well suited for use in the automated processing or analysis of physiological or biological samples such as blood. Accordingly, while the beneficial features and advantages of the present invention will be discussed in the context of blood collection tubes it should be emphasized that the present invention is not limited to blood analysis alone. Nonetheless, a discussion of the present invention in the context of multi-channel blood analyzer apparatus clearly illustrates the features and advantages of the present invention.

As previously detailed, early prior art automated analysis equipment typically requires a relatively skilled operator to introduce blood collection tubes to the instrument either individually or in multiple position racks or carrousels. As a result, the entire rack or carrousel of sample collection tubes must be moved as a unit and the analyzer must be provided with an additional mechanism to manipulate the carrousel and to process individual sample tubes. Moreover, when sample collection tubes of different sizes are introduced into these prior art analyzers, adapters or different size carrousels must be utilized to properly position the individual tubes for processing.

In contrast, the sample tube carrier of the present invention effectively eliminates the need to utilize supporting racks, carrousels and adapters and will handle a wide variety of sample collection tubes, cells or cuvettes without regard to shape, base configuration, diameter or length, within generally acceptable ranges. Of equal importance, the sample tube carriers of the present invention may be linked together to form conveniently handled multi-sample racks or magazines or, alternatively, linked to form chains of varying length.

These features are best illustrated in conjunction with the accompanying figures in which similar elements carry identical reference numbers. Turning first to the embodiment illustrated in FIGS. 1 through 9, FIGS. 1 and 2, demonstrate the ability of the sample tube carriers of the present invention to interface with automated sample tube processing apparatus. A plurality of linkable sample tube carriers 10,12 and 14 constructed in accordance with the teachings of the present invention are shown, each loaded with a specimen sample tube 16. Sample tube carriers 10,12,14 and other identical carriers are releasably linked together to form conveniently sized racks or magazines generally indicated by reference numerals 18,20,22 and 24. Preferably, racks 18 through 24 will be formed from four to six releasably linked individual sample tube carriers as this provides a rack of tube carriers that can be conveniently manipulated by hand if desired. However, alternatively sized racks or sample magazines may be configured depending upon size and need.

Figure 1:
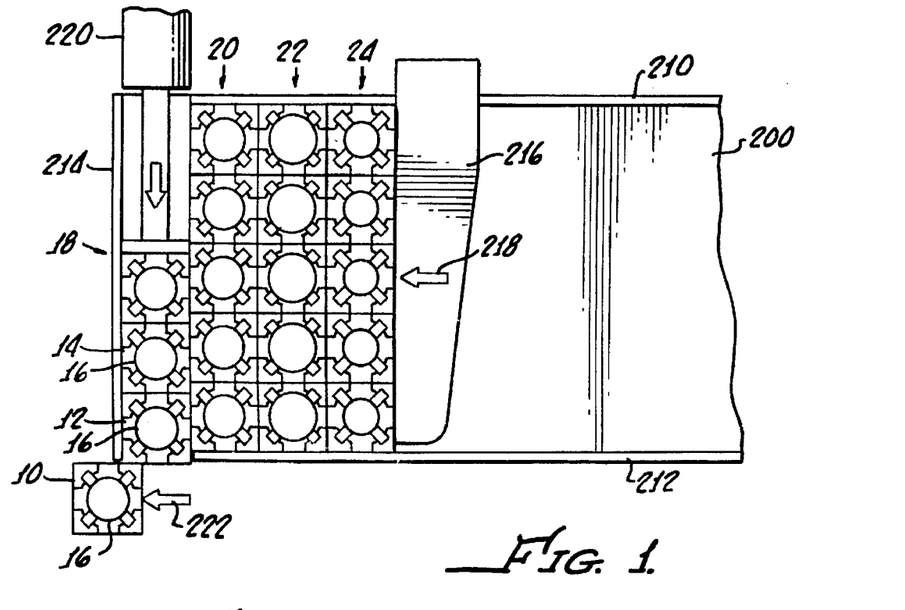
FIG. 1 is a plan view of an automated sample processing apparatus input tray loaded with a plurality of linkable sample tube carriers illustrating the adaptability and operation of the present invention.

As will be discussed in detail below, each individual rack is a stable, self-supporting unit that is easily maneuvered or manipulated as one piece. Moreover, as illustrated in FIG. 1 the unique configuration of the individual sample tube carriers produces racks that readily interface with one another so that a number of racks can be loaded into a processing or storage tray such as processing tray 200 of FIG. 1. Tray 200 is formed of a smooth horizontal base surface provided with vertical side walls 210 and 212 and an end wall 214. A movable sweeping partition or finger 216 forms the opposing end wall of tray 200. Movable partition 216 sweeps in the direction of arrow 218 to maintain racks 18,20,22 and 24 in a closed, indexed formation against one another and end wall 214. Thus, for storage purposes an operator simply loads a plurality of appropriately sized sample tube racks into tray 200 to form a snug, multi-sample array. Each sample tube 16 is retained securely in position relative to one another without fear of mishap, spilling or breakage because of the supporting interaction and spacing provided by each sample tube rack.

Similarly, to input each specimen sample into an automated processing apparatus movable partition 216 functions to sequentially feed complete racks into position against end wall 214. There plunger 220 progressively slides each rack (for example, rack 18 as shown in FIG. 1) past side wall 212 where the rack is progressively disassembled one sample tube carrier at a time so that each individual sample tube carrier and specimen sample tube assembly can function as an integral part of the automated handling and analyzing processes of the apparatus (not shown). Much in the way as each individual rack 18,20,22 and 24 is manipulated relative to one another by the simple horizontal sliding action provided by plunger 220, each sample tube carrier 10,12 and 14 is releasably linked or assembled/disassembled by its own horizontal motion relative to the remainder of its rack or adjacent carrier as shown by arrow 222.

As those skilled in the art will appreciate, preferably the sample tube carrier and specimen sample tube assembly remains together as it is handled and processed throughout the processing apparatus. However, if necessary the sample tube may be removed or reloaded with a simple vertical pulling or pushing motion. Upon completion of processing, the individual sample tube carrier/sample specimen tube assemblies may be reassembled into conveniently sized racks and reloaded into processing or storage trays in the reverse order. Thus, a simple horizontal sliding motion will link adjacent sample tube carriers to form racks which may be horizontally moved into close proximity with adjacent racks for convenient and secure storage or manipulation of large quantities of sample tubes.

Figure 2:
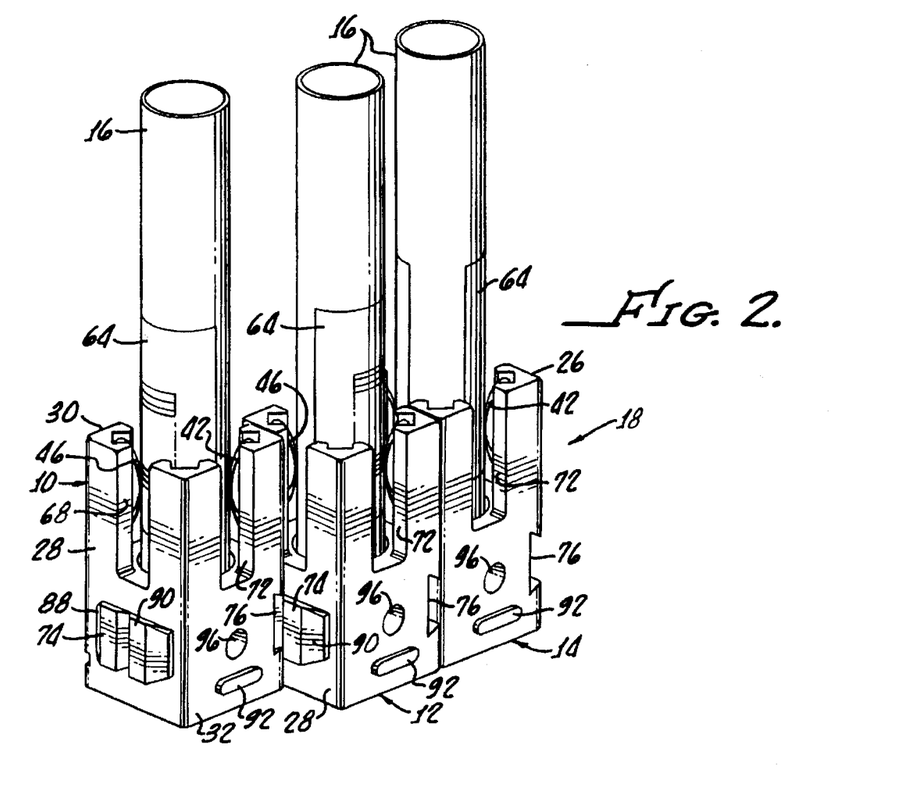
FIG. 2 is a perspective view of one linked rack of sample tube carriers further illustrating the releasably linking feature thereof.
Figure 3:
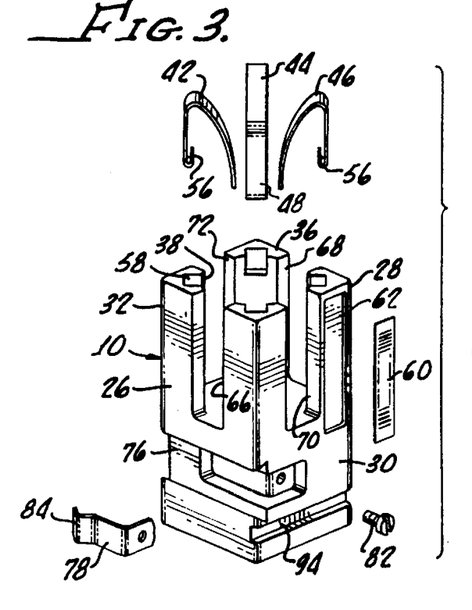
FIG. 3 is an exploded view of a linkable sample tube carrier illustrating an exemplary construction thereof.

The features of the sample tube carriers of the present invention which facilitate this ability to be conveniently manipulated both individually and in bulk are further illustrated in the exemplary embodiment of the sample tube carrier illustrated in FIGS. 2 and 3. Each carrier contains the necessary mechanical attributes to interface with other carriers as well as with the various tasks to be performed within the analyzer or processing apparatus. More specifically, the main body of each carrier 10 is formed as a longitudinally symmetrical, vertically oriented oblong polygonal body having a plurality of generally planar external side surfaces defined by at least two orthogonally or perpendicularly disposed pairs of opposed vertical rectangular faces 26,28, 30 and 32. The first pair of mutually opposed vertical rectangular faces is defined by vertical rectangular faces 26 and 28, and the second mutually opposed pair is defined by vertical rectangular faces 30 and 32.

Thus, in this exemplary embodiment of the present invention, oblong polygonal body 10 is a vertically oriented rectangle having four external side surfaces defined by rectangular faces 26,28,30 and 32. Though forming polygonal body 10 as a rectangle is preferred for ease of manufacturing and symmetry purposes, it should be emphasized that alternative polygonal shapes are contemplated as being within the scope of the present invention, including vertically oriented polygons having cross-sections formed of generally symmetrical triangles, pentagons, hexagons and the like. Regardless of the cross-sectional configuration, the polygonal body 10 is provided with a bottom sliding surface 34 which generally has a polygonal shape defined by the horizontal cross-section of the polygonal body 10. Preferably, as shown in FIGS. 4 through 9, bottom sliding surface 34 is substantially planar and smooth and is horizontally disposed so that the body of sample tube carrier 10 will sit securely on bottom sliding surface 34 yet be able to slide smoothly in a horizontal manner as discussed relative to FIG. 1. This construction enables the sample tube carriers of the present invention to remain stable for storage purposes yet to be smoothly manipulated in a horizontal sliding manner to interface with one another and to interface with processing apparatus chutes, channels, carriers and the like (not shown).

The top surface 36 of carrier 10 (shown in FIGS. 2 and 3) is preferably a smooth, generally planar horizontal surface provided with a central bore 38 defining a vertical cavity 40 which extends along the vertical longitudinal axis 54 of carrier 10 from top surface 36 to a point above bottom sliding surface 34. In this manner, vertical cavity 40 will extend along a portion of the longitudinal extent of the polygonal body of sample tube carrier 10. Again, it should be noted that while it is preferred that vertical cavity 40 terminate at a position above bottom sliding surface 34, this feature is not essential. Thus, it is within the scope of the present invention to continue bore 38 completely through sample tube carrier 10 if desired. Such an alternative construction of sample tube carrier 10 would facilitate photometric analysis of the contents of sample tube 16 along a vertical axis.

An important aspect of the present invention is the ability of vertical cavity 40 to releasably receive specimen sample tube 16. In addition to means for releasably receiving and retaining sample tube 16 in a generally vertically aligned position within vertical cavity 40, sample tube carrier 10 is also provided with self-adjusting positioning means for retaining sample tube 16 as well as self-centering means for aligning sample tube 16 to position tube 16 in a stable, generally vertically aligned, centered position within vertical cavity 40.

This centering of tube 16 along vertical axis 54 facilities the consistent and repeatable withdrawal of specimen sample aliquots from tube 16. As known in the art, the majority of automated analyzer apparatus utilize a descending sample probe to aspirate a portion of the sample contained in tube 16. Drawing the sample aliquot from the center of tube 16 is the most accurate way to perform this function because it avoids the problems of uneven flowrate that may occur if an aspirating probe is positioned close to the tube wall. As noted above, prior art attempts at sample tube centering generally require apparatus specific sample tubes as the adjustable sample tube carriers known in the art typically utilize lateral spring biasing devices that, depending on tube size, push the tube to the side of the carrier rather than to the center.

In the exemplary embodiment of the present invention, the self-adjusting positioning means for releasably receiving and retaining sample tube 16 is formed of a plurality of generally opposed spring biasing members 42,44,46 and 48 which are clearly illustrated in FIGS. 3, 7, 8 and 9. Each spring biasing member 42,44,46 and 48 extends into vertical cavity 40 from a position generally adjacent to top surface 36 about central bore 38 at an angle away from the periphery of vertical cavity 40. Thus, by extending the spring biasing members angularly down into vertical cavity 40 the opposed springs provide sample tube carrier 10 with the ability to self-adjust in order to receive and retain a wide variety of sample tube shapes and configurations.

For example, the majority of contemporary sample specimen tubes are cylindrical, round or flat bottomed tubes having diameters ranging from 10 millimeters to 17 millimeters. Similarly, relatively standard sample tube lengths have evolved in the art ranging from approximately 55 millimeters to 110 millimeters. Thus, in the exemplary embodiment of the present invention opposed spring biasing members 42,44,46 and 48 are configured to adapt to sample tube sizes ranging from approximately 7 millimeters to 20 millimeters in diameter.

Additionally, because the sample tube carriers are configured to slide conveniently along horizontal surfaces with the tubes in a vertical position the overall length of the specimen tubes does not effect their positioning within each sample tube carrier. Thus, specimen tube length is only limited by the configuration of the sample processing apparatus to be utilized rather than by the sample tube carriers of the present invention.

Further, as those skilled in the art will appreciate, by utilizing at least four opposed spring biasing members the sample tube carriers of the present invention can adapt to specimen tubes having cross-sectional configurations other than circular. Though relatively uncommon, non-circular specimen tubes such as rectangular or faceted cells or cuvettes are readily accommodated by the sample tube carriers of the present invention. Along these lines, it should be noted that four spring biasing members are not essential to the practice of the present invention. Rather, at least two and preferably at least three spring biasing members will achieve the desired self-adjusting positioning function of the present invention.

Figures 5, 8:
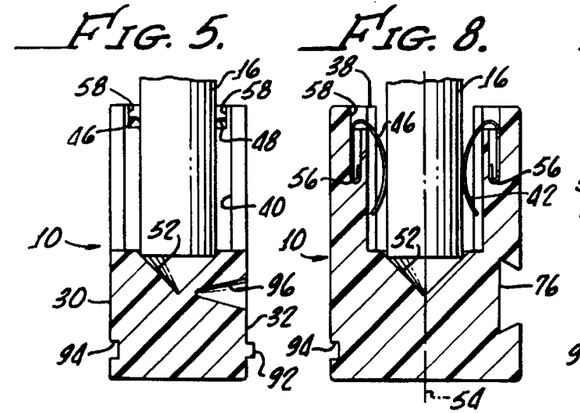
FIG. 5 is a vertical cross-section taken through the plane 5—5 of FIG. 4 illustrating additional features of the present invention.
FIG. 8 is a vertical cross-section taken along the plane 8—8 of FIG. 7 illustrating the self-adjusting and self-centering features of the present invention.
Figure 9:
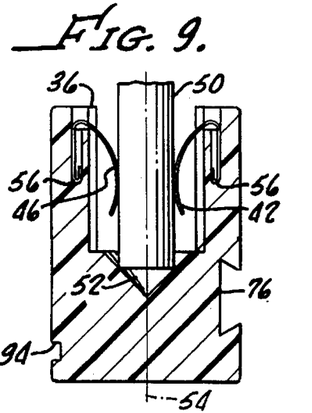
FIG. 9 is a vertical cross-section similar to that of FIG. 8 illustrating the self-adjusting feature of the present invention.

The ability of the sample tube carrier of the present invention to accommodate differing sized specimen sample tubes illustrated in FIGS. 8 and 9 where specimen tube 16 in FIG. 8 has a considerably larger cross-sectional diameter than that of specimen tube 50 in FIG. 9. Because of the angular configuration of spring biasing members 42,44,46 and 48 and their generally arcuate configuration the spring biasing members readily adapt to hold and position each respective specimen sample tube 16 or 50 stably and securely within sample tube carrier 10.

To further secure the specimen sample tubes 16 and 50 in a stable, generally vertically aligned central position within vertical cavity 40, sample tube carrier 10 is also provided with self-centering means for aligning the base of the sample tubes. As shown in FIGS. 5, 8 and 9, this self-centering means for aligning is formed from a simple funnel shaped or conical depression 52 at the base of vertical cavity 40. Preferably, conical depression 52 will have a smooth symmetrical configuration tapering to a centrally disposed tip aligned with the vertical longitudinal axis 54 of vertical cavity 40. In this manner, the base of specimen sample tube 16 is centered along the vertical axis 54 by depression 52 operating in conjunction with the centered alignment of specimen sample tube 16 along vertical axis 54 provided above the base of tube 16 by opposed spring biasing members 42,44,46 and 48.

As result of the foregoing combination of self-adjusting positioning means and self-centering aligning means each sample tube is stably, yet releasably centered, aligned, positioned and retained within each sample tube carrier. Moreover, potentially dangerous projections which may snag clothing or machine surfaces as sample tube carriers are transported or processed are eliminated. This significantly enhances the safety and ease of operation of the sample tube carriers of the present invention.

Further safety and operational advantages are provided by this construction as well in that the specimen sample tubes are positioned within each sample tube carrier by a simple vertically aligned pressing motion where the specimen tube is inserted into central bore 38 and pressed down past spring biasing members 42,44,46 and 48 until the base of the sample tube securely engages depression 52. Removal of the sample tube is accomplished by simply grasping the tube and pulling upward. Thus, adapters, clips and retainers are eliminated without eliminating the ability of the sample tube carriers of the present invention to securely receive and retain sample tubes.

This construction also simplifies the manufacturing of the present invention with associated reductions in cost. For example, as shown in FIGS. 3 and 8, by configuring the sample tube carriers of the present invention to receive the specimen sample tubes in a vertical fashion within vertical cavity 40 each spring biasing member can be attached to a sample tube carrier by simply inserting a U-shaped tang 56 on the base of each spring biasing member into an appropriately dimensioned hole 58 formed in top surface 36 of sample tube carrier 10. The angular or arcuate shape of each biasing spring then functions to assist in the retention of each respective U-shaped tang 56 in its corresponding hole 58 against a relative vertical movement of a specimen sample tube being loaded or unloaded from the tube carrier.

Preferably, the spring biasing members of this embodiment will be formed of spring steel or other resilient material such as plastic, steel, stainless steel, copper alloy, or composites to enable each U-shaped tang 56 to more securely engage the plastic material forming the body of tube carrier 10. Other suitable materials as known in the art may be utilized to form the spring biasing members; however, these exemplary materials are preferred for reasons of manufacturing simplicity, effective operation, and reduced cost.

An additional feature of the present invention is the ability to machine track each sample tube carrier and its associated specimen sample tube. Accordingly, it is preferred that at least one of the opposed vertical rectangular faces 26,28,30 and 32 be provided with machine readable indicia such as the bar code strip 60 illustrated in FIG. 3. Preferably, bar code strip 60 will be securely affixed to at least one of the vertical rectangular faces forming the side surfaces of tube carrier 10 such as rectangular face 30 shown. Additionally, while it is contemplated that bar code strip 60 may be painted or embossed directly onto the side surface, for ease of manufacturing and to retain the ability to modify bar code identification, it is preferred that bar code strip 60 be adhesively secured to rectangular face 30 within a correspondingly sized depression 62 to prevent the edges of bar code strip 60 from peeling or catching on surfaces as tube carrier 10 is manipulated.

Because sample tube carrier 10 is symmetrical about its longitudinal vertical axis 54 it is possible to spin sample tube carrier 10 about axis 54 to facilitate machine reading of indicia 60 during processing operations. This same symmetry also facilitates the ability of sample tube carrier 10 to maneuver around bends and through intersections in processing apparatus pathways. Thus, it is possible to randomly load large numbers of sample tube carriers into such an apparatus which will then read and identify each sample tube carrier as it is processed.

Along these lines, though the specimen sample tubes 16 or 50 are not considered to be a part of the present invention, in order to facilitate the operation and tracking of individual specimen samples it is preferred that each tube 16 be provided with its own bar code strip 64 for use as illustrated in FIG. 2. It should be appreciated that bar code strip 64 on tube 16 alone is sufficient to identify each sample tube and sample tube carrier combination. Thus, bar code strip 60 on carrier 10 may be used as an adjunct to bar code strip 64 on tube 16. In order to reduce the sensitivity of the positioning of bar code strip 64 relative to sample tube carrier 10 it is preferred that each of the vertically oriented rectangular faces 26,28,30 and 32 be provided with a vertical slot, 66,68,70 and 72, respectively, which intersects vertical cavity 40 so that bar code strip 64 can be viewed from outside sample tube carrier 10. Thus, as shown in FIG. 2, the positioning of bar code strip 64 relative to the top surfaces 36 of sample tube carriers 10,12 or 14 is irrelevant to accurate machine reading. The same is true with respect to the lateral positioning of bar code strip 64 relative to each rectangular face. 26,28,30 and 32 of sample tube carriers 10,12 or 14. As long as the indicia of bar code strip 64 project into at least one of vertical slots 66,68,70 or 72 machine reading is possible.

In this manner, it is possible for the automated processing apparatus utilizing the sample tube carriers of the present invention to simultaneously read and identify each individual specimen sample tube and its corresponding sample tube carrier and to maintain this correspondence throughout the processing of each sample. The same tracking advantages can be achieved during storage of the sample specimen tubes and their associated sample tube carriers.

The ability of the sample tube carriers of the present invention to function independently or to interface with one another and/or the transport or storage mechanisms within automated processing apparatus is produced by the unique symmetry of their respective vertical axes in conjunction with their horizontally disposed bottom sliding surfaces and the ability of each carrier to horizontally engage and releasably link to adjacent carriers while being able to simultaneously slidingly engage and index orthogonally disposed adjacent carriers. Each of these horizontally engaging linking or sliding index functions is provided by its own mechanical structure incorporated into each linkable sample tube carrier.

Figure 4:
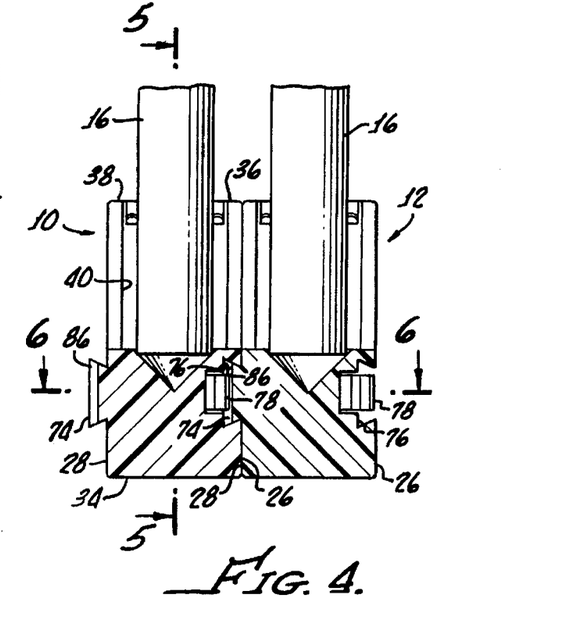
FIG. 4 is a vertical cross-section of two linked sample tube carriers illustrating the releasable locking feature.
Figure 6:
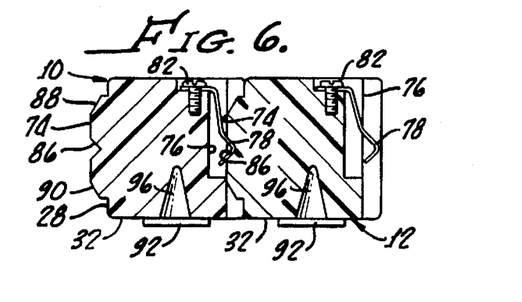
FIG. 6 is a horizontal cross-section of two linkable sample tube carriers taken along the plane 6—6 of FIG. 4.
Figure 7:
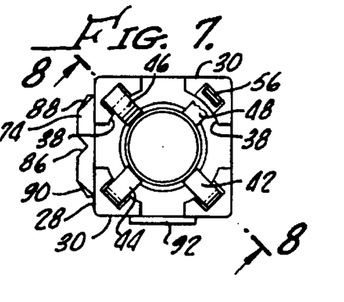
FIG. 7 is a top view of a single sample tube carrier.

More specifically, the preferred means for horizontally engaging and releasably linking adjacent carriers is provided on the first pair of opposed vertical rectangular faces 26 and 28. As illustrated in FIGS. 2, 4 and 6, the horizontally engaging and releasably linking means comprises a horizontally aligned enlarged head projection such as dovetail member 74 projecting from one of the first pairs of opposed vertical faces, in the embodiment shown, vertical rectangular face 28. In this context, the term "horizontally aligned" means that the enlarged head of dovetail member 74 is enlarged in the vertical direction as shown in FIG. 4 such that each carrier 10 or 12 may slide horizontally with respect to one another but not vertically with respect to one another. The corresponding portion of the means for horizontally engaging and releasably linking is an aligned mating groove such as dovetail groove 76 provided in the second face of the first pair of opposed generally rectangular vertical faces, in the embodiment shown, vertical rectangular face 26. By providing a relative sliding motion between adjacent sample tube carriers 10 and 12, as illustrated in FIGS. 1 and 2, horizontally aligned dovetail member 74 projecting from face 28 of sample tube carrier 12 will engage with mating groove 76 formed in rectangular face 26 of sample tube carrier 10. Thus, it is seen that the dovetail member 74 and dovetail groove 76 provide the carriers 12 with cooperating means for engaging and releasably linking adjacent carriers with one another in response to horizontal relative sliding movement of the carriers along a horizontal line substantially parallel with the faces 26 and 28. The carriers 12 can thus be moved relatively to one another to an engaged and linked relative position of the carriers (see FIG. 4) in which the dovetail member and dovetail groove substantially prevent relative translational movements of the linked carriers 12 in all directions except along the horizontal line. Also, the engaged dovetail member and dovetail groove of the carriers so linked substantially prevents relative pivotal motions about both a vertical axis between the linked carriers, as well as about a horizontal axis extending through both of the linked carriers.

Further, as shown in FIGS. 3, 4 and 6, it is preferred that dovetail groove 76 be provided with a spring biasing means for releasably locking the dovetail member 74 of the adjacent sample tube carrier. More specifically, this releasable locking feature is provided by biasing spring 78 which is mounted in a horizontal depression 80 in dovetail groove 76 with screw 82. Biasing spring 78 in turn is provided with a vertically aligned projection 84 which engages a correspondingly shaped and positioned detent 86 in dovetail member 74. This engagement is clearly shown in the horizontal cross-section of FIG. 6 and in the vertical cross-section of FIG. 4. To facilitate the horizontally sliding engagement of the spring biased releasable lock provided by biasing spring 78, dovetail member 74 is provided with beveled vertical edges 88 and 90.

The combination of the horizontally engaging dovetail interface with the spring biased releasable lock provides these exemplary sample tube carriers of the present invention with the ability to link into the previously discussed racks, magazines or chains in a stable, self supporting arrangement; yet, each individual sample tube carrier may be separated from its adjacent tube carriers by a simple perpendicularly aligned horizontal sliding motion. As those skilled in the art will appreciate, these same interlocking features may be utilized to engage each carrier with correspondingly configured structures in a sample processing apparatus conveyor or transport system (not shown) to securely, yet releasably, mount each sample tube carrier and its associated specimen tube in such apparatus for automated processing.

Additional storage and operational stability is provided to the sample tube carriers of the present invention by the previously mentioned horizontally engaging sliding means for indexing adjacent carriers. Preferably, this sliding means for indexing will be provided in the second pair of opposed vertical rectangular faces, in the present embodiment rectangular faces 30 and 32, to avoid conflict with the sliding function of the perpendicularly disposed releasable linking means. In the embodiment shown, the horizontally engaging sliding means for indexing is formed from a horizontally aligned member 92 projecting from rectangular face 32 as shown in FIGS. 2, 5, 6, and 7. Unlike dovetail member 74, horizontally projecting member 92 need not be provided with an enlarged head. Rather, a uniform or outwardly tapering cross-section is preferred as this facilitates the smooth horizontally sliding indexing function of horizontal member 92 with its correspondingly aligned horizontal groove 94 provided in its opposed vertical rectangular face 30 as adjacent carriers or racks are pushed along one another.

For example, referring back to FIGS. 1 and 2, when rack 18 moves horizontally relative to rack 20 the horizontal members 92 projecting from sample tube carriers 10, 12 and 14 will engage the correspondingly aligned horizontal grooves in the linked sample tube carriers of rack 20. Because the indexing means is not provided with a releasably locking spring biasing structure the individual sample tube carriers or racks are free to slide horizontally relative to one another with the added stability against tipping or misalignment provided by the horizontally sliding engaging function of horizontally projecting members 92 and corresponding horizontal grooves 94. This indexing interface functions to stabilize groupings of sample tube carrier racks as shown in FIG. 1 as well as the relative horizontal motion of each rack or sample tube carrier. Moreover, by providing correspondingly engaging structures in the conveyors, chutes or tubes of an automated processing apparatus (not shown) an added degree of stability and security can be provided. For example, the horizontally sliding indexing function will prevent tipping of individual sample tube carriers as they are pushed, assembled or disassembled as illustrated in FIG. 1.

To facilitate the alignment of the sample tube carriers during assembly, disassembly or horizontal sliding transport, it is preferred that at least one of the rectangular faces 26,28,30 or 32 be provided with an indexing notch 96. As shown in FIGS. 2, 5, and 6, it is preferred that indexing notch 96 be provided in rectangular face 32 as this provides a very positive linkup with automated assembly and disassembly plungers such as that represented by arrow 222 in FIG. 1. For this reason, it is preferred that indexing notch 96 be of a generally conical or self-centering configuration so that a horizontally operating plunger may securely index the sample tube carrier and avoid tipping or cocking of the carrier as horizontal force is applied to overcome the spring biasing provided by the releasable locking biasing spring 78. Along these lines, to assist further in the prevention of vertical rocking, tipping or cocking, it is preferred that in this embodiment bottom sliding surface 34 be formed as a smooth, generally planar, horizontally disposed square surface.

Figure 10:
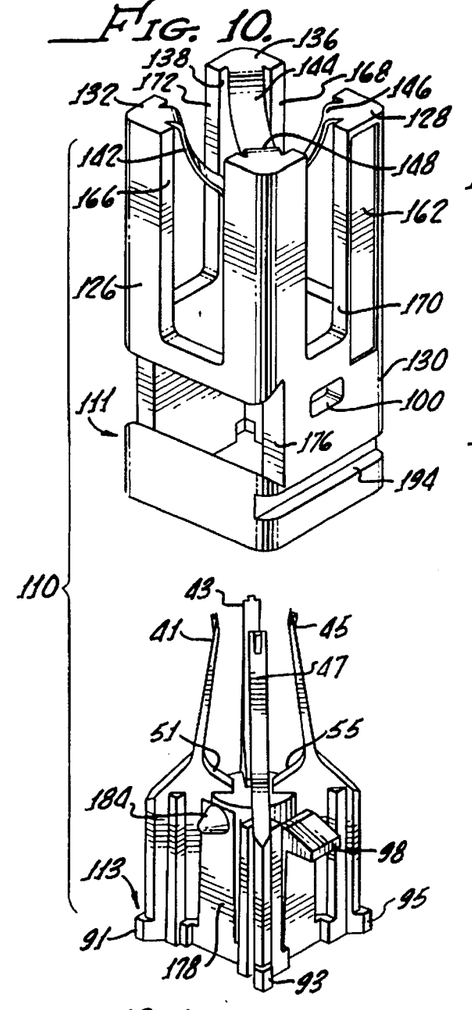
FIG. 10 is an exploded perspective view of a multi-piece alternative embodiment of the present invention.

An alternative embodiment of the present invention is illustrated in FIGS. 10 through 13. This alternative embodiment incorporates the same functional elements in a unique two-part or multi-piece structure having its own attendant advantages. Accordingly, to facilitate the identification of common structural features and elements between the two embodiments of the present invention shown, similar features of this alternative embodiment will bear the same reference numerals with the prefix "100". Thus, as illustrated in FIG. 10 the exemplary alternative sample tube carrier 110 is formed of a polygonal body configured from two interlocking subunits, outer body member 111 and inner body member 113. The exploded construction of sample tube carrier 110 illustrated in FIG. 10 produces the same functional features as that previously discussed with respect to carrier 10 of FIG. 3 but with considerably fewer separately assembled elements. Thus, as with carrier 10, outer body member 111 of carrier 110 forms the longitudinally symmetrical, vertically oriented oblong polygonal body having a plurality of generally planar external side surfaces defined by at least two orthogonally disposed pairs of opposed vertical rectangular faces 126, 128, 130 and 132. The first pair of mutually opposed vertical rectangular faces is defined by faces 126 and 128 and the second mutually opposed pair is defined by faces 130 and 132.

Figure 11:
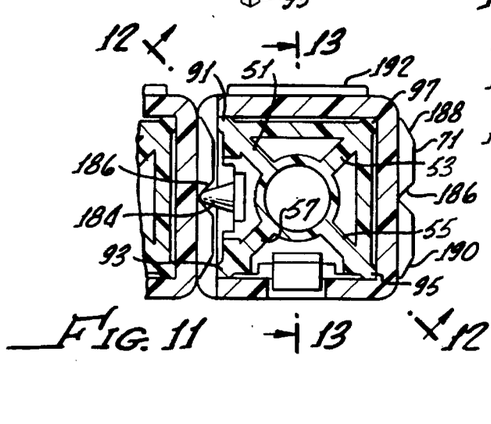
FIG. 11 is a horizontal cross-section taken along the plane 11—11 of FIG. 13 illustrating the assembly and indexing of the multi-piece body components.
Figure 12:
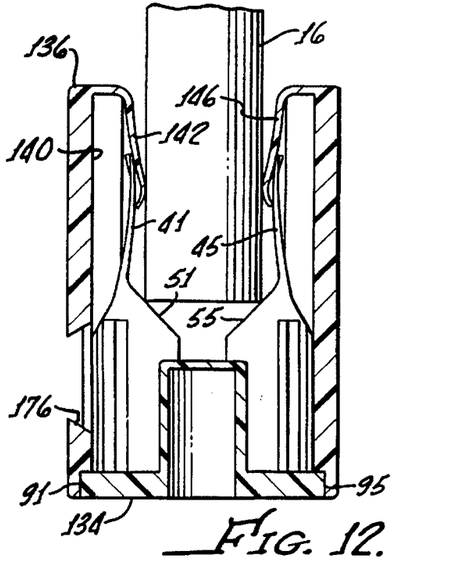
FIG. 12 is a vertical cross section taken along the plane 12—12 of FIG. 11 illustrating the self-adjusting and self-centering features of the alternative embodiment.
Figure 13:
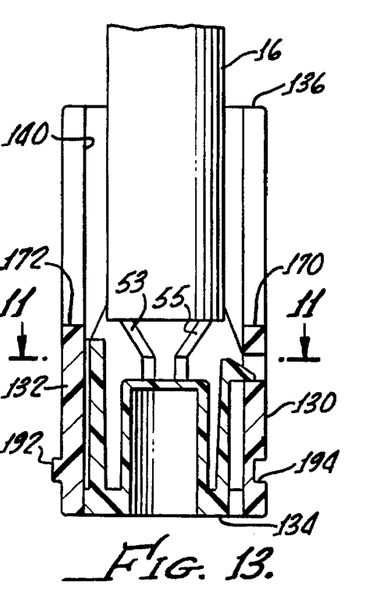
FIG. 13 is a vertical cross section taken along the plane 13—13 of FIG. 11 illustrating the assembly and features of the alternative embodiment of the present invention.

Similarly the top surface 136 of carrier 110 is a smooth, generally planar horizontal surface provided with a central bore 138. Because of the two-element construction of alternative sample tube carrier 110 the vertical cavity 140 defined by central bore 138 is considerably more open than that of previously discussed sample tube carrier 10. In effect, outer body member 111 is hollow and the configuration of vertical cavity 140 is defined by the structural interconnection achieved when inner body member 113 is locked into position within outer body member 111 as shown in FIGS. 11, 12, and 13. This interlocking engagement is accomplished by locking member 98 of inner body member 113 which is biased to engage hole 100 in outer body member 111 which operates in conjunction with projecting feet 91, 93, 95, and 97 to securely lock inner body member 113 within outer body member 111.

Like sample tube carrier 10, sample tube carrier 110 is provided with self-adjusting positioning means for reasonably receiving and retaining sample tube 16. However, unlike the individual spring biasing members 42, 44, 46 and 48 of sample tube carrier 10, sample tube carrier 110 is provided with double or compound spring biasing members formed of outer spring biasing members 142, 144, 146 and 148 integral to outer body member 111 and inner biasing spring members 41, 43, 45 and 47 integral to inner body member 113.

This configuration of the opposed spring biasing members provides several advantages. First, the compound spring biasing members resist deformation or loosening that may result over time from cold flow of the spring material when under stress. Additionally, because inner and outer body members 111 and 113 can be formed of different materials each compound spring can be provided with elements having different spring factors. Thus, inner spring biasing members 41, 43, 45, and 47 can be made of relatively stiff material while outer spring biasing members 142, 144, 146, and 148 can be made of a softer, more accommodating, self lubricating material. Similarly, less expensive plastic materials can be utilized to form the larger structures of outer body member 111 where material strength is less critical. Further, assuming that sample tube carrier 110 is made of plastic this construction will eliminate the utilization of relatively expensive metals which may rust. Further manufacturing economies are achieved by eliminating the multiple parts and their associated manufacturing and assembly costs.

Sample tube carrier 110 also is provided with self-centering means for aligning the base of sample tube 16. In this embodiment of the present invention the self-centering means is formed from a plurality of inclined planes 51, 53, 55, and 57 sloping toward the center of vertical bore 140. As shown in FIGS. 12 and 13, inclined planes 51, 53, 55, and 57 engage the base of specimen sample tube 16 and center it along the vertical axis of sample tube carrier 110. These centrally intersecting inclined planes function in the same manner as the funnel shaped or conical depression 52 of sample tube carrier 10, yet do so with considerably less material.

Sample tube carrier 110 also is provided with a depression 162 in vertical rectangular face 130 to hold a bar code strip (not shown) if desired. Additionally, vertical slots 166, 168, 170 and 172 are provided in vertical rectangular faces 126, 128, 130 and 132, respectively, so that a bar code strip on sample tube 16 can be viewed from outside carrier 110.

Smooth, generally planar bottom horizontal sliding surface 134 is formed by the base of inner body member 113.

Though functionally identical to the horizontally engaging and releasable linking means of sample tube carrier 10, the unique construction of alternative sample tube carrier 110 produces a horizontally engaging and releasable linking means formed of one or more outwardly projecting, mutually angularly opposed, horizontally aligned engagement surfaces defining an enlarged head or dovetail projection. Because of their mutually outward angulation, these surfaces function in a manner identical to that of dovetail member 74 of sample tube carrier 10 but with less material. Thus, as illustrated in FIG. 11, upper engagement member 71 defines the top surface of the enlarged head projection and its parallel opposite surface disposed directly below it (not visible) defines the bottom surface a dovetail provided on rectangular face 128 which slidingly engages dovetail groove 176 provided in vertical rectangular face 126. Engagement member 71 is provided with a detent 186 and bevelled vertical edges 188 and 190. As shown in FIG. 11, detent 186 is engaged by projection 184 on integral biasing spring 178 to form a releasable locking feature to securely link the horizontally engaged dovetail interfaces of adjacent sample tube carriers.

Similarly, as with sample tube carrier 10, sample tube carrier 110 is provided with horizontally engaging sliding means for indexing adjacent carriers. Thus, vertical rectangular face 130 is provided with a horizontal groove 194 and vertical rectangular face 132 is provided with a correspondingly aligned horizontal projecting member 192. Thus, alternative sample tube carrier 110 functions in essentially the identical manner as that of the previously discussed embodiment.

By eliminating the need for fixed size carrousels or racks the sample carriers of the present invention provide an added degree of operating flexibility that was not available in the art. Varying numbers of samples can be processed conveniently and individual sample runs may be interrupted for "stat" tests without changing carrousels or unloading the processing apparatus. Similarly, broken or damaged sample tubes can be "pulled" from their carriers without interruption of the overall process.

As previously noted, the polygonal body of the sample tube carrier of the present invention is preferably formed of inexpensive materials such as plastic or metal. Thus, polyvinylchloride, polycarbonate, polypropylene polysulfone, acetate, cellulose and other suitable materials may be utilized to form the sample tube carriers through casting, injection molding, investment molding, machining or other suitable techniques. It should be emphasized that the longitudinal symmetry of the preferred embodiments of the present invention is particularly suitable for injection molding or casting manufacturing techniques. This greatly simplifies the manufacturing process and reduces the associated expense. However, other materials and manufacturing techniques may be utilized as required for the intended operating environment. Thus, higher temperature compatible or higher load compatible sample tube carriers may be formed from composite materials or metals as needed. In this context, it should be emphasized that the functions and dimensions discussed herein are exemplary only and that alternative dimensions may be utilized within the scope and teaching of the present invention.

Thus, in closing, it is to be understood that the embodiments of the invention disclosed herein are illustrative of the principles of the invention and that other modifications may be employed within the scope thereof. Accordingly, the present invention is not limited to that precisely as shown and described in the present specification.

We claim:

1. A linkable sample tube carrier, comprising:
   a longitudinally symmetrical vertically oriented oblong polygonal body having a plurality of generally planar external side surfaces defined by at least two orthogonally disposed pairs of substantially vertically oriented generally rectangular opposed faces;
   a generally horizontally disposed polygonal bottom sliding surface; and
   a top surface having a substantially centered bore defining a longitudinally disposed vertical cavity extending along at least a portion of the longitudinal extent of said body and adapted to releasably receive the sample tube, a first pair of said two pairs of opposed faces including cooperating means for engaging and releasably linking said carrier with an adjacent carrier in response to horizontal relative movement of one of said carrier and the adjacent carrier along a horizontal line substantially parallel with said first pair of faces, so that when engaged and linked said cooperating means substantially prevents relative translational movements of said carriers in all horizontal directions except along said line, and also substantially prevents relative pivotal motion about both a vertical axis between said carriers, as well as about a horizontal axis extending through both of said carriers; and a second pair of said two pairs of opposed faces including sliding means for indexing said carrier with an adjacent carrier or with a sample tube processing apparatus.

2. The carrier of claim 1 wherein each of said substantially vertically oriented generally rectangular opposed faces is provided with a vertical slot intersecting said vertical cavity and extending along at least a portion of the length of said cavity.

3. The carrier of claim 1 further comprising machine readable indicia disposed upon at least one of said external side surfaces.

4. The carrier of claim 1 wherein said cooperating means comprises at least one horizontally aligned enlarged head member projecting from one of said generally rectangular opposed faces of said first pair of opposed faces and a correspondingly aligned and configured mating groove provided in the other generally rectangular opposed face of said first pair of opposed faces.

5. The carrier of claim 1 wherein said sliding means comprises a horizontally aligned member projecting from one of said generally rectangular opposed faces of said second pair of opposed faces and a correspondingly aligned horizontal groove provided in the other generally rectangular opposed face of said second pair of opposed faces.

6. The carrier of claim 1 further comprising self-adjusting positioning means for releasably receiving and retaining a sample tube in a stable generally vertically aligned position within said vertical cavity.

7. The carrier of claim 6 wherein said self-adjusting positioning means comprises a plurality of generally opposed spring biasing members, each of said spring biasing members extending angularly down into said vertical cavity from a position adjacent to the periphery of said substantially centered bore in said top surface to a position within said vertical cavity.

8. The carrier of claim 6 wherein said self-adjusting positioning means further comprises self-centering means for aligning the sample tube within said vertical cavity.

9. The carrier of claim 8 wherein said self-centering means comprises a funnel shaped depression forming a base of said vertical cavity.

10. The carrier of claim 8 wherein said self-centering means comprises a plurality of inclined planar surfaces sloping toward the center of said bore.

11. The carrier of claim 1 wherein said polygonal body is a rectangle.

12. The carrier of claim 11 wherein said polygonal bottom sliding surface is a square.

13. The carrier of claim 4 wherein said mating groove is provided with a spring biasing means for releasably locking at least one projecting enlarged head member of an adjacent carrier in mating engagement.

14. A linkable sample tube carrier, comprising:
a vertically oriented oblong polygonal body having a plurality of generally planar external side surfaces defined by two orthogonally disposed pairs of substantially vertically oriented generally rectangular opposed faces, a first pair of said two pairs of opposed faces including cooperating means for engaging and releasably linking said carrier with an adjacent carrier in response to horizontal relative movement of said carrier and the adjacent carrier along a horizontal line substantially parallel with said first pair of faces to an engaged and linked relative position of said carriers in which said cooperating means substantially prevents relative translational movements of said carriers in all directions except along said line, and also substantially prevents relative pivotal motion about both a vertical axis between said carriers, as well as about a horizontal axis extending through both of said carriers; and a second pair of said two pairs of opposed faces including sliding means for indexing said carrier with an adjacent carrier;
a generally horizontally disposed planar rectangular bottom sliding surface; and
a top surface provided with a central bore defining a vertical cavity extending along at least a portion of the longitudinal axis of said body, said cavity adapted to releasably receive and retain a sample tube.

15. The carrier of claim 14 wherein each of said substantially vertically oriented generally rectangular opposed faces is provided with a vertical slot intersecting said vertical cavity and extending along at least a portion of the length of said cavity.

16. The carrier of claim 14 further comprising machine readable indicia disposed upon at least one of said external side surfaces.

17. The carrier of claim 14 wherein said cooperating means comprises at least one horizontally aligned enlarged head member projecting from one of said generally rectangular opposed faces of said first pair of opposed faces and a correspondingly aligned and configured mating groove provided in the other generally rectangular opposed face of said first pair of opposed faces.

18. The carrier of claim 14 wherein said sliding means comprises a horizontally aligned member projecting from one of said generally rectangular opposed faces of said second pair of opposed faces and a correspondingly aligned horizontal groove provided in the other generally rectangular opposed face of said second pair of opposed faces.

19. The carrier of claim 14 further comprising self-adjusting positioning means for releasably receiving and retaining a sample tube in a stable generally vertically aligned position with said vertical cavity.

20. The carrier of claim 19 wherein said self-adjusting positioning means comprises a plurality of generally opposed spring biasing members, each of said spring biasing members extending angularly down into said vertical cavity from a position adjacent the periphery of said substantially centered bore in said top surface to a position within said vertical cavity.

21. The carrier of claim 19 wherein said self-adjusting positioning means further comprises self-centering means for aligning the sample tube within said vertical cavity.

22. The carrier of claim 21 wherein said self-centering means comprises a plurality of inclined planes forming a base of said vertical cavity.

23. The carrier of claim 17 wherein said mating groove is provided with spring biasing means for releasably locking at least one enlarged head member of an adjacent carrier in mating engagement.

24. A linkable sample tube carrier, comprising:
a vertically oriented rectangular body having a vertically extending longitudinal axis and external side surfaces defined by two orthogonally disposed pairs of substantially vertically oriented generally rectangular opposed faces, each of said faces provided with a vertical slot extending along at least a portion of the length of said rectangular body, the first pair of said two pairs of opposed faces including cooperating means for engaging and releasably linking said carrier with an adjacent carrier in response to horizontal relative movement of said carrier and the adjacent carrier along a horizontal line substantially parallel with said first pair of faces, so that when engaged and linked said cooperating means substantially prevents relative translational movements of said carriers in all vertical directions and in all horizontal directions except along said line, and also substantially prevents relative pivotal motion about both a vertical axis between said carriers, as well as about a horizontal axis extending through both of said carriers; and the second pair of said two pairs of opposed faces including sliding means for indexing said carrier with an adjacent carrier;
a horizontally disposed planar bottom sliding surface;
a top surface having a central bore defining a vertical cavity longitudinally extending along at least a portion of said longitudinal axis of said body and provided with a funnel shaped depression at a base of said vertical cavity;
self-adjusting positioning means for releasably receiving and retaining a sample tube in a stable, vertically aligned position within said vertical cavity; and
machine readable indicia disposed upon at least one of said faces.

25. A linkable sample tube carrier, comprising:
a vertically oriented rectangular body having a vertically extending longitudinal axis and external side surfaces defined by two orthogonally disposed pairs of substantially vertically oriented generally rectangular opposed faces, each of said faces provided with a vertical slot extending along at least a portion of the length of said rectangular body, the first pair of said two pairs of opposed faces including cooperating means for engaging and releasably linking said carrier with an adjacent carrier in response to horizontal relative sliding movement of one of said carrier and the adjacent carrier along a horizontal line substantially parallel with said first pair of faces so that a face of said first pair slidably engages the other face of said first pair of faces of the adjacent carrier to engage and link the carriers and said cooperating means of the linked carriers substantially prevents relative translational movements of said carriers in all directions except along said line, and also substantially prevents relative pivotal motion about both a vertical axis between said carriers, as well as about a horizontal axis extending through both of said carriers; and the second pair of said two pairs of opposed faces including sliding means for indexing said carrier with an adjacent carrier;

a horizontally disposed planar bottom sliding surface;

a top surface having a central bore defining a vertical cavity longitudinally extending along at least a portion of said longitudinal axis of said body and provided with a funnel shaped depression at a base of said vertical cavity;

self-adjusting positioning means for releasably receiving and retaining a sample tube in a stable, vertically aligned position within said vertical cavity; and machine readable indicia disposed upon at least one of said faces;

wherein said cooperating means comprises a horizontally aligned enlarged head or dovetail member projecting from one of said generally rectangular opposed faces of said first pair of opposed faces and a correspondingly aligned mating dovetail groove provided in the other generally rectangular opposed face of said first pair of opposed faces;

whereby said carrier and an adjacent carrier may be releasably linked by sliding at least one of said carrier and the adjacent carrier at said bottom sliding surface so that the enlarged head or dovetail member of one carrier slides into releasably locked mating engagement with the correspondingly aligned dovetail groove of the other carrier.

26. The carrier of claim 25 wherein said sliding means comprises a horizontally aligned member projecting from one of said generally rectangular opposed faces of said second pair of opposed faces and a correspondingly aligned horizontal groove provided in the second generally rectangular opposed face of said second pair of opposed faces.

27. The carrier of claim 25 wherein said self-adjusting positioning means comprises a plurality of generally opposed spring biasing members, each of said spring biasing members extending angularly down into said vertical cavity from a position adjacent the periphery of said substantially centered bore in said top surface to a position within said vertical cavity.

28. The carrier of claim 25 wherein said mating dovetail groove is provided with spring biasing means for releasably locking the enlarged head or dovetail member of an adjacent carrier in mating engagement.

* * * * *